United States Patent [19]

November

[11] 3,956,922

[45] May 18, 1976

[54] DENSITOMETER PROBE SHIELD AND WELL

[75] Inventor: Milton H. November, Hacienda Heights, Calif.

[73] Assignee: International Telephone and Telegraph Corporation, New York, N.Y.

[22] Filed: Feb. 10, 1975

[21] Appl. No.: 548,276

Related U.S. Application Data

[63] Continuation-in-part of Ser. No. 530,943, Dec. 9, 1974, abandoned, which is a continuation-in-part of Ser. No. 528,870, Dec. 2, 1974, abandoned, which is a continuation-in-part of Ser. No. 470,528, May 16, 1974, abandoned.

[52] U.S. Cl. ............................................. 73/32 A
[51] Int. Cl.² ........................................ G01N 9/00
[58] Field of Search ............. 73/32 A, 32 R, 194 B, 73/204

[56] References Cited
UNITED STATES PATENTS

| | | | |
|---|---|---|---|
| 2,414,370 | 1/1947 | Floyd | 73/349 |
| 3,246,515 | 4/1966 | Martino et al. | 73/204 |
| 3,677,067 | 7/1972 | Miller et al. | 73/32 |
| 3,719,080 | 3/1973 | Burgess | 73/194 |

*Primary Examiner*—Herbert Goldstein
*Attorney, Agent, or Firm*—A. Donald Stolzy

[57] ABSTRACT

A vibration densitometer probe with a shield and well which have solved a calibration shift problem involving a calibration shift that occurred when the probe was placed in different gases or in the hollow interiors or pipelines of different sizes or geometries or the probe was placed in the same container or pipeline with different orientations. Unusual shield perforations and ports also improve operation.

14 Claims, 15 Drawing Figures

DENSITOMETER PROBE SHIELD AND WELL

BACKGROUND OF THE INVENTION

This application is a continuation-in-part of a third copending application Ser. No. 530,943 filed Dec. 9, 1974 now abandoned. Said third application is a continuation-in-part of a second copending application Ser. No. 528,870 filed Dec. 2, 1974 now abandoned. Said second application is, in turn, a continuation-in-part of a first copending application Ser. No. 470,528 filed May 16, 1974 now abandoned. The benefit of the filing dates of said first, second and third applications is therefore hereby claimed for the subject matter therein common to this application.

This invention relates to densitometers, and more particularly, to vibration densitometer probe accessories.

In the past, a vibration densitometer would take a frequency calibration shift when used in different environments. This has been a very serious problem because recalibration is time consuming, requires expert personnel and is often required at an inconvenient place, i.e. in the field.

It has also been impossible to obtain good accuracy over a broad range in the use of conventional vibration densitometers. Perplexing phase shifts and other phenomena not traceable have caused inaccuracies. At times, a vibration densitometer has completely failed to achieve lock or has "lost lock." A vibration densitometer is essentially an electromechanical oscillator. When it fails to oscillate, the densitometer is commonly described as failing to achieve lock or losing lock.

Vibration densitometer accuracy has also been impaired by the pitot (ram pressure) effect, turbulence and other undesirable flow characteristics.

Still further, high amplitude flow noise has prevented or made extremely difficult the operation of conventional vibration densitometers.

In the past, vibration densitometer outputs have had erroneous readings over large flow rate ranges in pipelines. The same is true over large density ranges. Further, prior art vibration densitometers have had troublesome temperature instability and unduly long start-up times.

SUMMARY OF THE INVENTION

In accordance with the present invention, the above-described and other disadvantages of the prior art are overcome by providing a probe shield with or without means providing a further enclosure for the vibrating member of a vibration densitometer.

The shield of the present invention has outstandingly met the long felt and serious need to solve the calibration shift problem.

The shield of the present invention has also increased densitometer accuracy over a broad range.

Undesirable phase shifts have also been eliminated by the use of the shield of the present invention.

Further, the shield of the present invention has saved denistometers from losing lock.

In addition to the foregoing, the shield of the present invention overcomes the ram effect, turbulence and other problems of vibration densitometers caused by these and other flow characteristics including, but not limited to, high amplitude flow noise.

The combination of the shield and enclosure means has increased density and flow rate ranges, has increased temperature stability, and has decreased start up time.

The above-described and other advantages of the present invention will be better understood from the following detailed description when considered in connection with the accompanying drawings.

BRIEF DESCRIPTION OF THE DRAWINGS

In the drawings which are to be regarded as merely illustrative.

DESCRIPTION OF THE PREFERRED EMBODIMENTS

Figure 1:
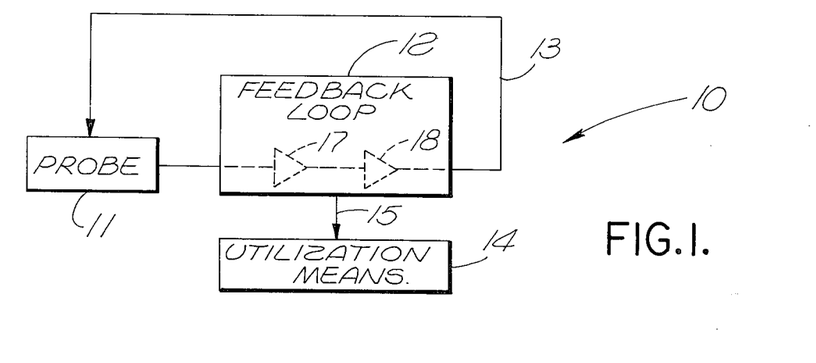
FIG. 1 is a block diagram of a vibration densitometer.

In FIG. 1, a vibration densitometer 10 is shown including a probe 11, a feedback loop 12 connected from and to probe 11 via a lead 13, and utilization means 14 connected from another output 15 of loop 12. Densitometer 10 may be identical, if desired, to that disclosed in U.S. Pat. No. 3,677,067. Attention is also invited to U.S. Pat. No. 3,741,000. By this reference hereto, the entire contents of both of these patents are hereby incorporated in their entireties herein hereat.

Figure 8:
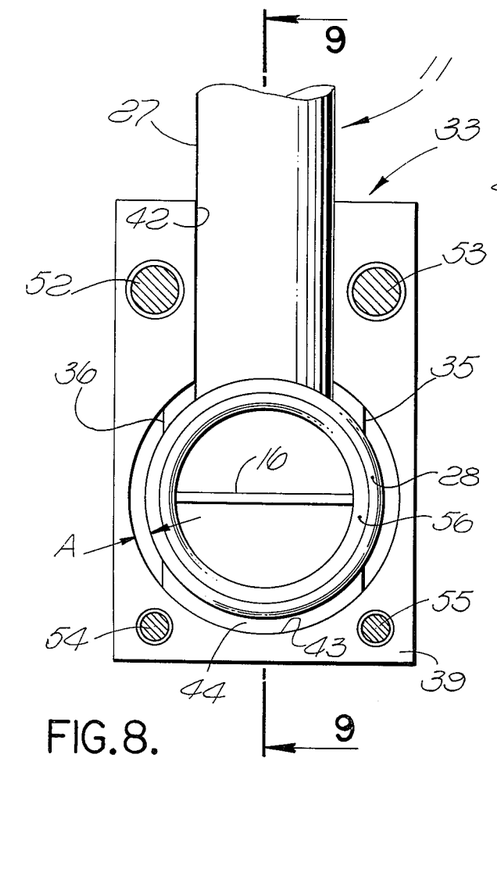
FIG. 8 is a vertical elevational view similar to that shown in FIG. 6 with the vibration densitometer probe inserted in one-half of the probe shield.

Probe 11 contains a vane 16 shown in FIG. 8 which is vibrated. Vane 16 is vibrated because the probe has a piezoelectric crystal pick-up, not shown, the output of which is amplified and the vane 16 vibrated by a magnetostrictive driver, not shown. The resonant vibrational frequency of vane 16 is a known function of the density of the gas or liquid or other flluid in which the vane 16 is immersed.

If desired, loop 12 in FIG. 1 may have a linearization circuit so that the output signal on lead 15 may have a magnitude directly proportional to density.

Utilization means 14 may be a voltmeter or ammeter calibrated in density, a process controller, a gas flow computer, a net oil computer or otherwise.

In accordance with the foregoing, the word "densitometer" is hereby defined to include or not include utilization means 14. Note will be taken that the densitometer in many cases will be manufactured and sold without any utilization means 14. Such utilization means 14 would be supplied by the customer.

The vibration densitometer 10 is essentially an electrochemical oscillator. The oscillator obviously has losses. Loop 12, therefore, includes at least one amplifier. Two amplifiers 17 and 18 are illustrated in loop 12 in FIG. 1.

Figure 2:
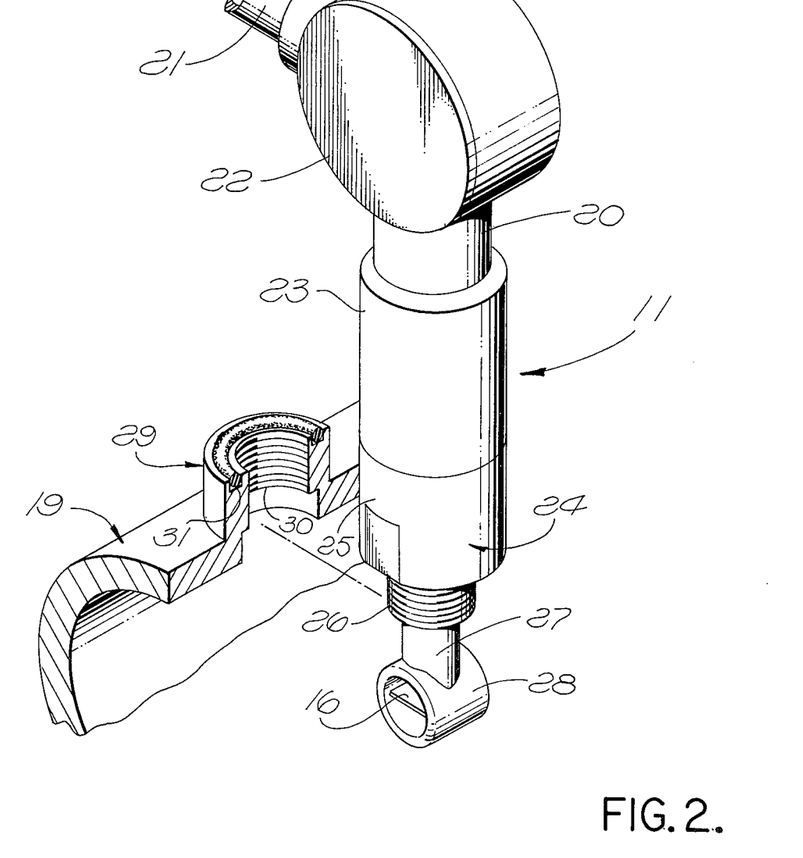
FIG. 2 is an exploded perspective view of a vibration densitometer probe, a portion of its mount and a portion of a pipeline.

Probe 11 is shown again in FIG. 2 for mounting in a pipeline 19.

Densitometer 10 may, alternatively, be, if desired, identical to that diclosed in said U.S. Pat. No. 3,741,000.

The probe 11 may be identical to the probe shown in the said U.S. Pat. No. 3,741,000 with certain exceptions. All these exceptions are noted hereinafter.

The said U.S. Pat. No. 3,741,000 is referred to hereinafter as the "later" patent.

The probe 11 is identical to the probe of the said later patent except for the addition of conduits 20 and 21, and a pull box 22. Conduits 20 and 21 and pull box 22 simply serve as enclosures for the output leads from probe 11 to loop 12 shown in FIG. 1.

Conduit 21 is threaded to pull box 22 in a manner not shown. Conduit 20 is threaded to pull box 22 and to a body 23 of probe 11. Conduits 20 and 21, pull box 22 and body 23 are, thus, all fixed together. A body 24 is fixed to body 23. Body 24 has an upper portion 25 of a larger diameter and a lower portion 26 of a smaller diameter that is externally threaded. A shank 27 is fixed to threaded portion 26 and to a cylinder 28. Vane 16 is mounted in a fixed position along its opposite edges to cylinder 28, as shown in both FIGS. 2 and 8.

Pipeline 19 has a hollow cylindrical projection 29 permitting probe 11 to be lowered thereinto, projection 29 having an axis perpendicular to the axis of pipeline 19. Projection 29 is internally threaded at 30. Probe portion 26 is threaded into projection 29 at the thread 30. Projection 29 has an O-ring groove 31, and an O-ring 32 therein that seals with a shoulder, not visible in FIG. 2, at the bottom of probe portion 25 where the diameter of the probe is reduced to the diameter of the threaded portion 26 thereof. The bottom surface of the probe portion 25 may be flat and in a plane perpendicular to the vertical axis of the probe 11 so as to rest on O-ring 32, O-ring 32 thereby sealing probe 11 inside pipeline 19. At least that portion of probe 11 below the thread 26, thus, protrudes downwardly inside pipeline 19 below the inside diameter thereof.

All the structure shown in FIGS. 1 and 2 may be entirely conventional, if desired.

In accordance with the present invention, the structures of FIGS. 1 and 2 are modified by placing a shield around shank 27 and cylinder 28. Both halves of the shield are substantially identical. One-half of the shield is indicated at 33 in FIG. 3. Shield half 33 has a generally cylindrical external surfae at 34. However, this cylindrical surface is interrupted by vertical slots 35 and 36. Holes 37 and 38 extend perpendicularly completely through shield half 33. Holes 37 and 38 have axes which are normal to a flat surface 39. Holes at 40 and 41 similarly have axes perpendicular to surface 39 and go completely through shield half 33.

Figure 3:
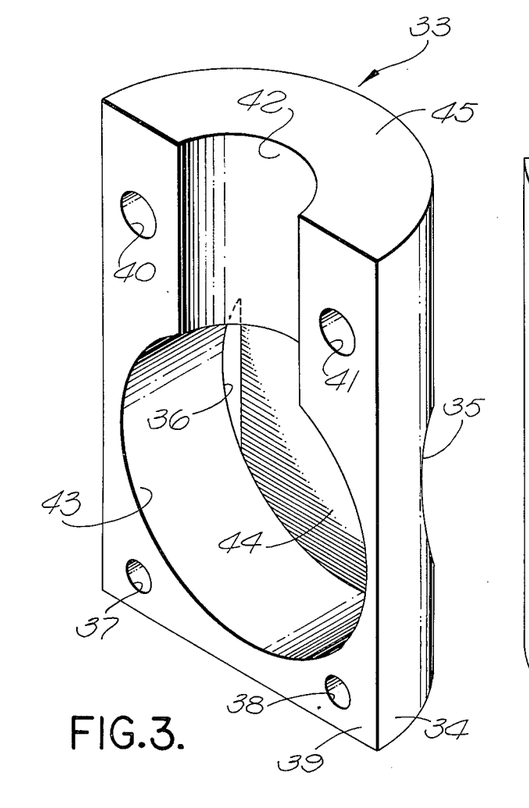
FIG. 3 is a perspective view of one-half of a probe shield constructed in accordance with the present invention, both halves of the probe shield being substantially identical.

The holes 37 and 38 are somewhat smaller than the holes 40 and 41. However, all of the holes 37, 38, 40 and 41 serve the same purpose. An Allen head screw is positioned in each of the holes 37, 38, 40 and 41 to hold the two shield halves together. The screws for the holes 37 and 38 cause surface 39 therebetween to abut the corresponding surface in the other shield half.

Shiel half 33 has a vertical half bore 42 which may be slightly smaller than the diameter of shank 27 so that the screws of holes 40 and 41 can clamp both shield halves against shank 27 and hold the shield in a fixed position relative thereto.

Shield half 33 has another partial cylindrical bore 43, the axis of which is normal to the axis of the bore 42. Bore 43 terminates in a flat surface 44 which is generally circular except for the slots 35 and 36. Surface 44 is parallel to surface 39.

In manufacture, the openings 35 and 36 are conveniently provided at the same time that bore 43 is provided in that the bore 43 is extended to an extent such that the boring tool interrupts the external surface 34 of shield half 33 and thereby provides the apertures 35 and 36. However, boring is stopped short of going completely through the shield half 33 leaving material, one surface of which is illustrated at 44.

Figure 4:
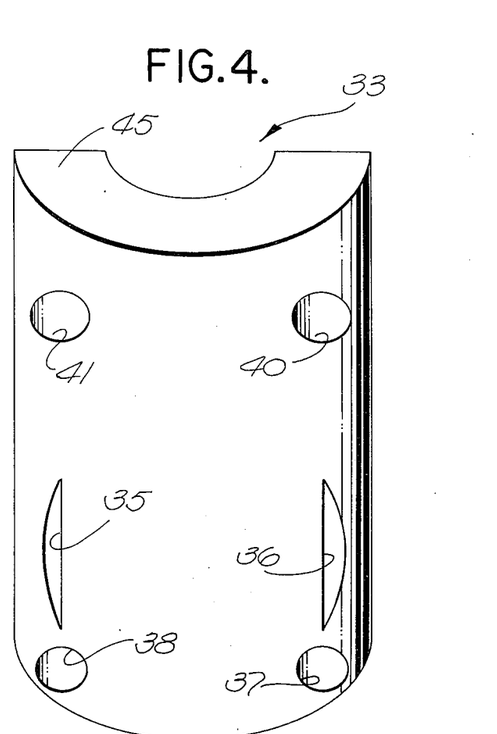
FIG. 4 is another perspective view of the probe shield shown in FIG. 3.

Shield half 33 is again shown in FIG. 4. Note will be taken in both of the FIGS. 3 and 4 that shield half 33 has an upper flat surface 45 which is generally semi-circular and lies in a plane perpendicular to the axis of bore 42.

Figure 5:
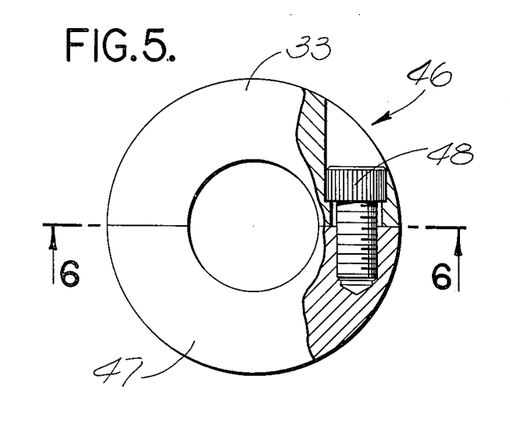
FIG. 5 is a top plan view of the probe shield, partly in section.

The entire shield is illustrated at 46 in FIG. 5. Shield half 33 is shown in FIG. 5 with the other shield half 47. A typical Allen head screw 48 is shown in FIG. 5. All four of the screws may be identical except for their diameters.

Figure 6:
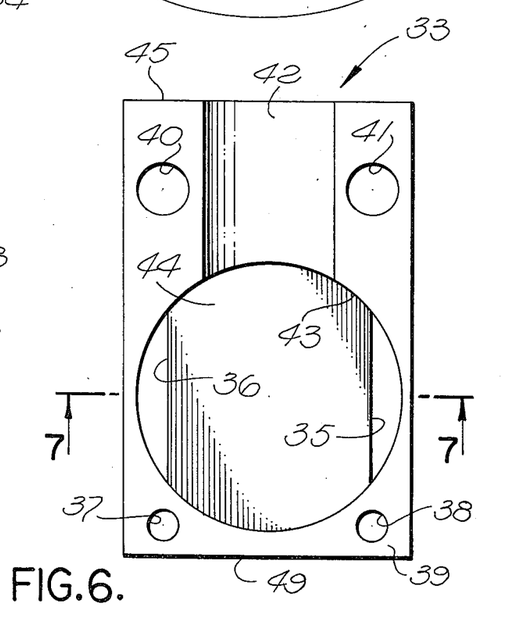
FIG. 6 is an elevational view of a probe shield half taken generally in the direction of the line 6—6 shown in FIG. 5.

Shield half 33 is again shown in FIG. 6. Note that the upper and lower surfaces 45 and 48, respectively, of shield half 33 in FIG. 6 are flat and parallel. Surface 49 has the exact shape of one-half of a circle.

Figure 7:
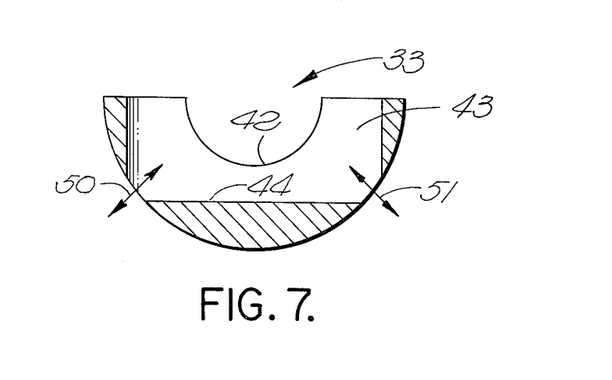
FIG. 7 is a transverse sectional view of the probe shield half taken on the line 7—7 shown in FIG. 6.

Shield half 33 is again shown in FIG. 7 having openings allowing ingress and egress of fluid in the direction of arrows 50 and 51.

In FIG. 8, screws are shown at 52, 53, 54 and 55. The view of FIG. 8 is quite similar to the view of FIG. 6 with shield 46 clamped onto probe shank 27. Shield half 33 is shown in FIG. 8.

In FIG. 8, note will be taken that a cylinder 56 is fixed inside cylinder 28. This construction is described in the said U.S. Pat. No. 3,677,067. Cylinders 28 and 56 are substantially the same length and are substantially flush at each of their opposite ends. They are somewhat rounded at each of their opposite ends.

In FIG. 8, note will be taken that cylinder 28 is everywhere a distance A from bore 43. However, shield halves 33 and 47 are clamped tightly upon probe shank 27, as shown in both FIGS. 8 and 9.

In FIG. 9, probe 11 is shown again with shield halves 33 and 47 clamped tightly to probe shank 27. Shield half 47 has one opening indicated at 56.

Figure 9:
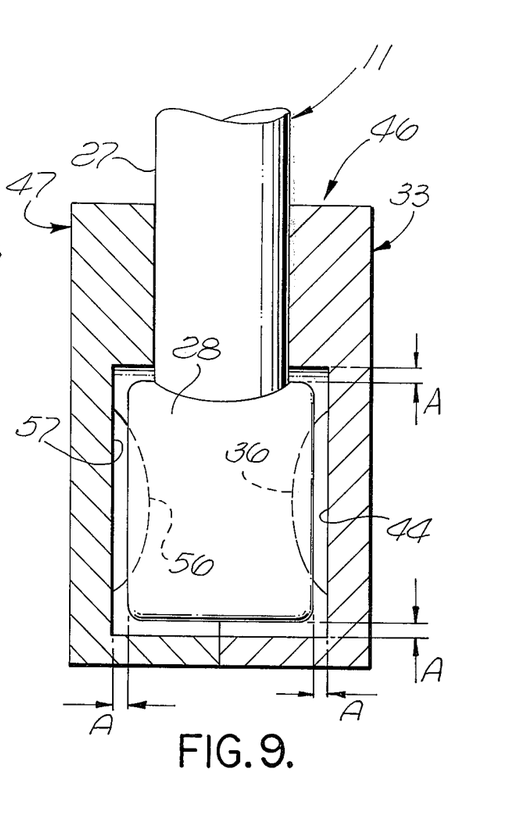
FIG. 9 is a vertical sectional view, partly in elevation, taken on line 9—9 of the structure shown in FIG. 8.

In FIG. 9, it will be noted that except for the three openings 35, 36 and 56, and the fourth symmetrical one, not shown, shield 46 encases an assembly which includes cylinder 28 and vane 16. The same is not fluid tight except for openings 35, etc., but it may be fluid tight, and it allows very little fluid flow into or out of the shield 46 except for the apertures 35, etc.

Again, in FIG. 9, note will be taken that cylinder 28 is spaced from surface 44, a corresponding surface 57 of shield half 47, and completely around the external surface of cylinder 28 as shown in both FIGS. 8 and 9, and as shown at A in both FIGS. 8 and 9.

Although probe 11 may or may not be made of heavier materials such as stainless steel, shank 27, cylinder 28 and cylinder 56 may be made of stainless steel. Vane 16 may be made of Ni-Span-C. Shield 46 need not necessarily be made of a lighter material and need not necessarily be made of aluminum, but is preferably made of aluminum.

Figures 10, 11, 12:
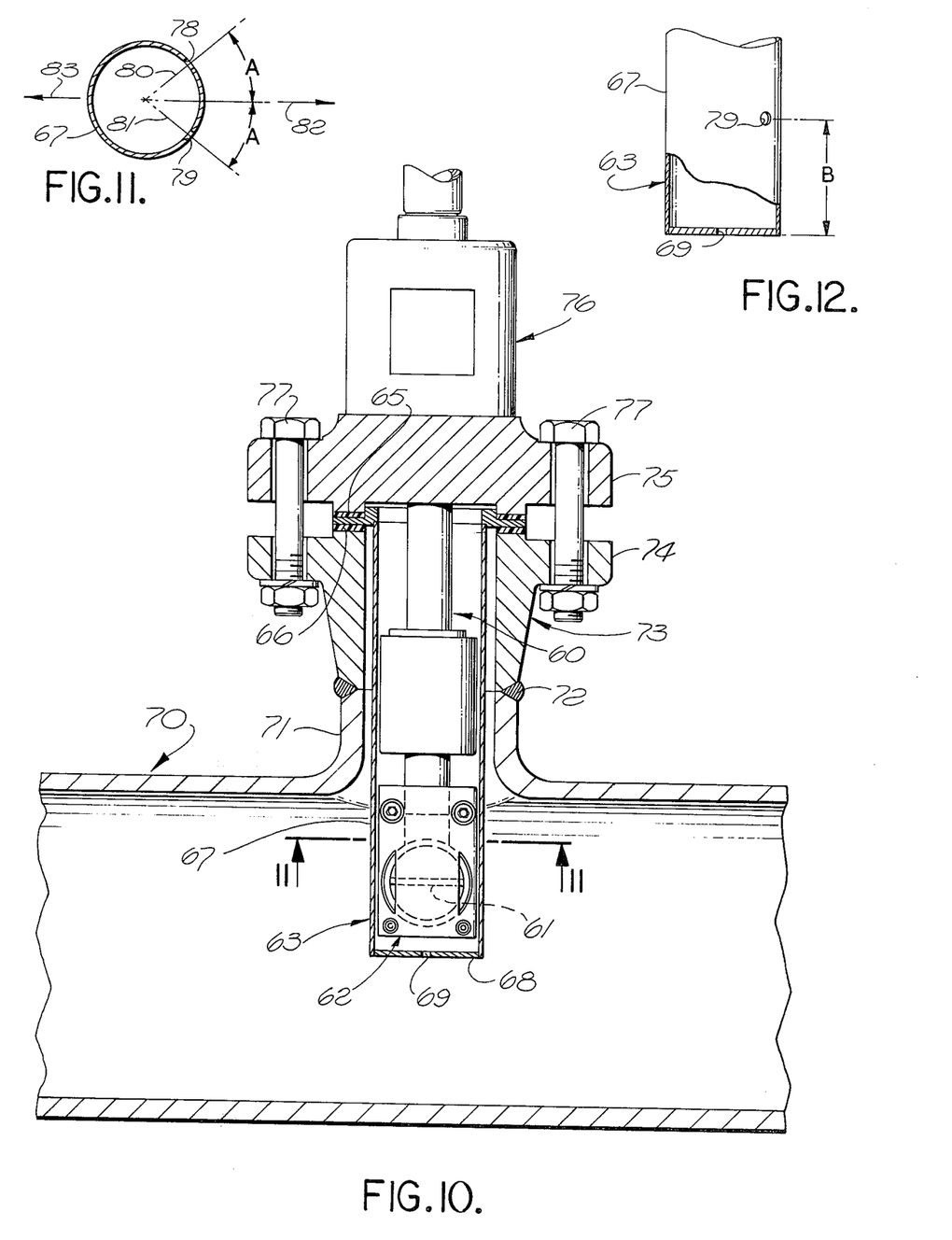
FIG. 10 is a vertical sectional view, partly in elevation, through a pipeline having a shielded densitometer probe mounted in a well therein in accordance with the present invention.
FIG. 11 is a horizontal sectional view through the well taken on the line 11—11 shown in FIG. 10.
FIG. 12 is a broken away elevational view of the well.

A modification of the invention is illustrated in FIG. 10. FIG. 10 includes a densitometer probe 60 having a vane 61 and a shield 62 located in a well 63. Well 63 is formed of a ring 64 having annular gaskets 65 and 66 bonded on opposite sides thereof. A cylinder 67 then has an upper open end sealed to ring 64 and a disk 68 sealing the lower end thereof except for a fluid exit hole 69.

A pipeline is illustrated at 70 having a hollow cylindrical projection 71 which is welded at 72 to a fitting 73 that has a flange 74 bolted to a flange 75 of an assembly 76 at preferably three or more or, for example, eight places 77.

As shown in FIG. 11, cylinder 67 has circular holes 78 and 79 through the wall thereof. Holes 78 and 79 have axes 80 and 81, respectively, disposed at an angle A' of 40° relative to the direction of fluid flow in pipeline 70. This fluid flow may be in either one of the directions indicated by arrows 82 or 83.

Each of the holes 78 and 79 may have their respective axes 80 and 81 located in a horizontal plane perpendicular to the axis of cylinder 67 a distance B from the bottom of cylinder 67 as indicated in FIG. 12, where B is 2.25 inches. The dimensions shown in FIG. 12 are not critical, but are typical.

Figure 13:
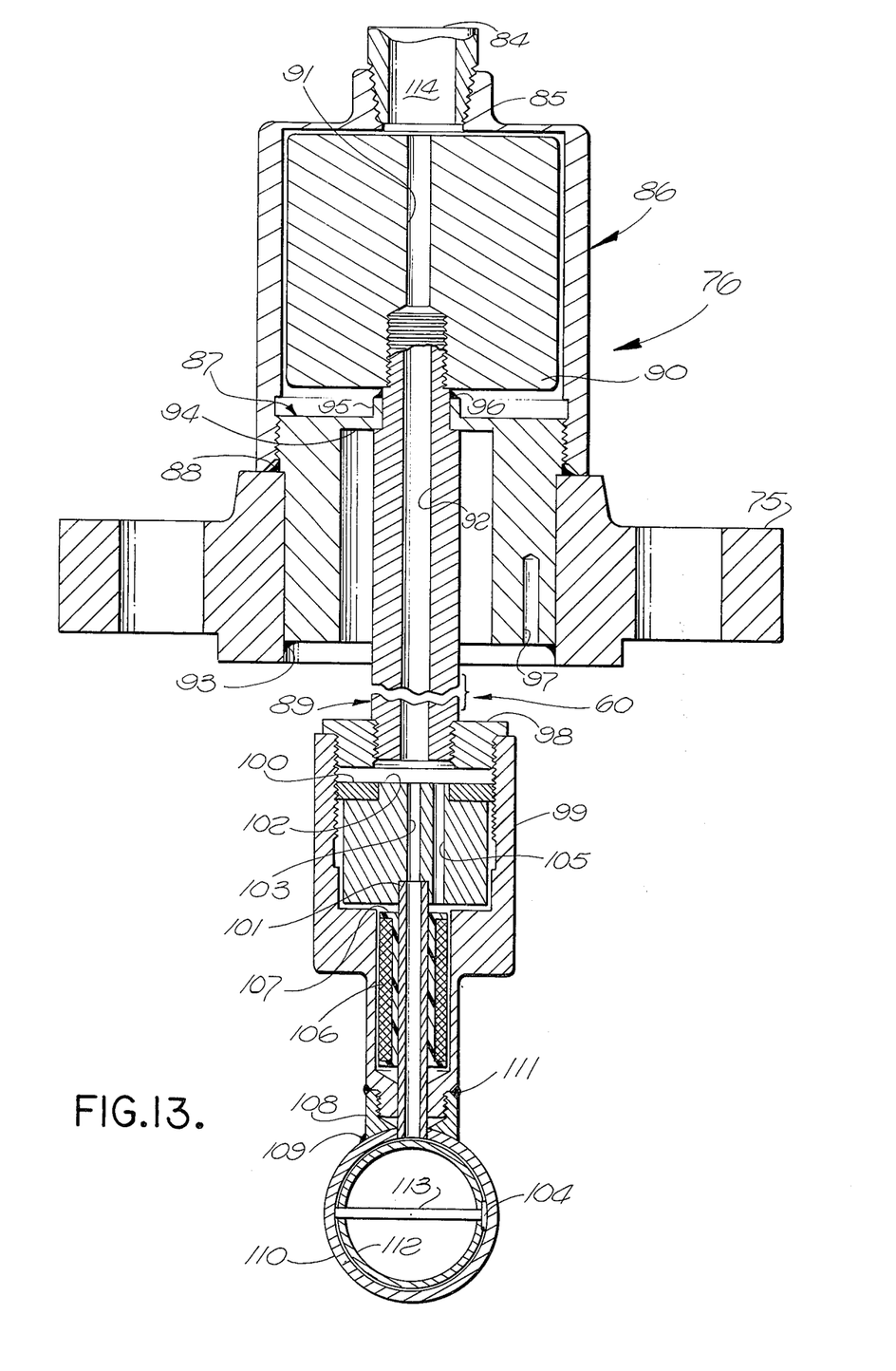
FIG. 13 is a vertical sectional view through the densitometer probe illustrated in FIG. 10.

A vertical sectional view of probe 60 is shown in FIG. 13 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 that is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pin hole 97, if desired, so that it may be held while end cap 86 is turned or threaded thereto.

Shaft 89, is, in turn, fixed to a ferrule 98 by being threaded thereinto. Ferrule 98, in turn, is fixed to a body 99 by being threaded thereinto.

A ring 100 is threaded into body 99. A magnetostrictive tube 101 which is hollow and open at both ends is press fit into a body 102. Body 102 is similar to a body disclosed in the said U.S. Pat. No. 3,741,000, and may be identical thereto, if desired. Alternatively, body 102 may have one hole 103 to receive lead wires from a piezoelectric crystal 104, and a hole 105 to receive lead wires from a drive coil 106 wound on a dielectric spool 107 press fit onto tube 101. A ferrule 108 is welded at 109 to a cylinder 110. Body 99 is threaded into ferrule 108 and welded thereto at 111. Tube 101 extends, at the bottom thereof, through a circular hole in cylinder 110 and bears against the external cylindrical surface of a cylinder 112. A vane 113 is fixed inside cylinder 110 in a manner identical to that illustrated in the said U.S. Pat. No. 3,677,067. The same is true of crystal 104.

The utility of a vibration densitometer employing the structure disclosed herein is described in detail in the last mentioned patent. The embodiment of the invention illustrated in FIGS. 10, 11, 12 and 13 has additional utility in that erroneous readings are avoided over large density and flow rate ranges. This embodiment also has superior temperature stability over that of the prior art, and has an unusually short start up time compared to the start up times of prior art of vibration densitometers.

Cylinders 110 and 112, vane 113, and crystal 104 may be identical to those disclosed in the last mentioned patent, if desired. Tube 101 is slidable through the lower end of body 99 and is slidable through the said circular hole through cylinder 110, as is known from the said last mentioned patent.

A more detailed explanation of the operation of a vibration densitometer employing the structure disclosed herein is set forth in the said last mentioned patent.

It is common to use a preamplifier in the probe. Such a preamplifier may be employed at 114 in FIG. 13, or at any other convenient location, as desired.

Figure 14:
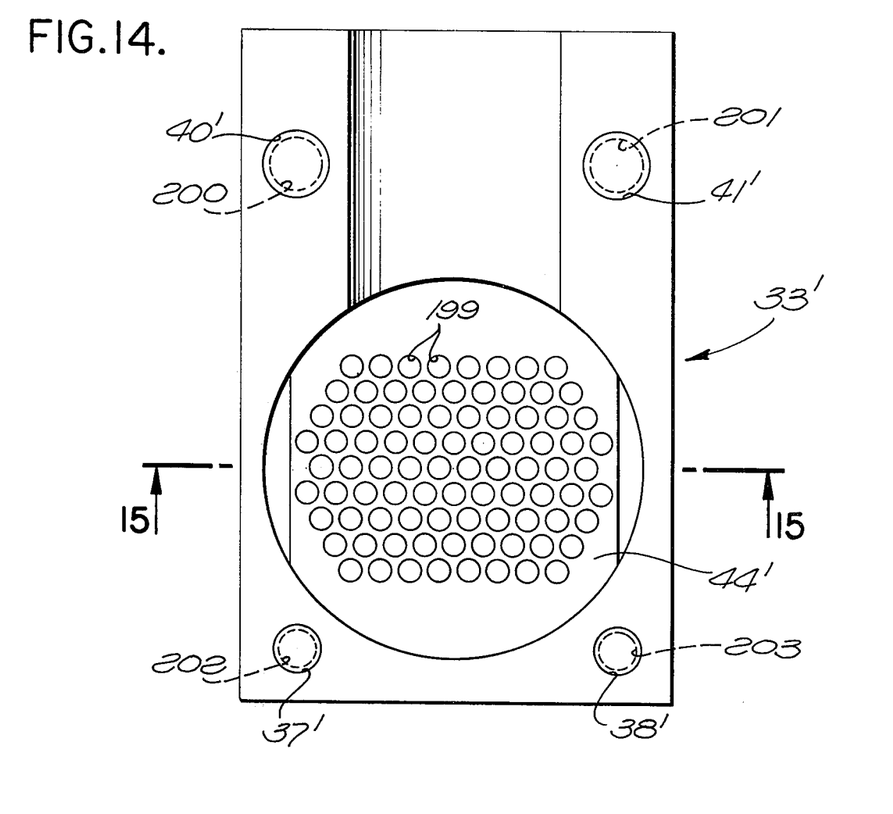
FIG. 14 is a side elevational view of one-half of a probe shield constructed in accordance with the present invention.

FIG. 14 is a view identical to that illustrated in FIG. 6 except for the enlargement thereof and the addition of holes 199 which extend completely through the portion of a shield half 33' normal to a flat surface 44' which may, if desired, be identical to surface 44 shown in FIG. 6.

Shield half 33' is a half of a shield of an alternative construction of the present invention.

If desired, shield half 33' may have holes 40', 41', 37' and 38' identical to holes 40, 41, 37 and 38 shown in FIG. 6.

The half of the shield to mate with shield half 33' would, in elevation, look identical to shield half 33' except for the same differences illustrated in FIG. 5. For example, a section taken on the line C—C in FIG. 5 would look the same as shield half 33' in FIG. 14 except that holes 40', 41', 37' and 38' would be omitted, and holes at 200, 201, 202 and 203 would be provided. Holes 199 or similar holes would be provided in both shield halves, of which shield half 33' would be a portion.

Figure 15:
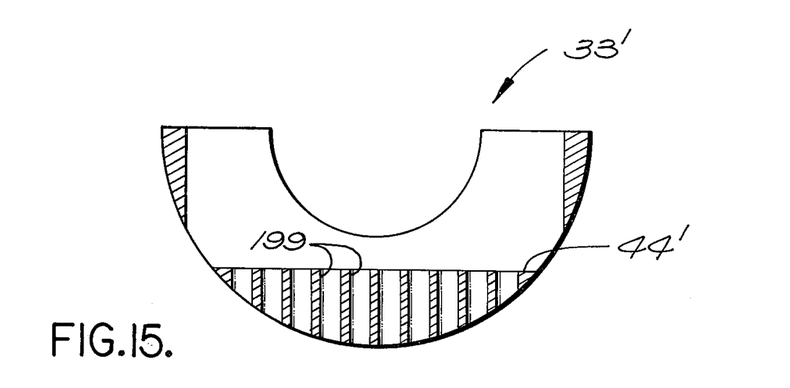
FIG. 15 is a transverse sectional view of the probe shield taken on the line 15—15 in FIG. 14.

Note holes 199 in FIG. 15.

All the dimensions given herein are typical, but are not substantially critical. The diameters of holes 199 are preferably kept within the limits as set forth hereinafter.

Typically, holes 199 are located symmetrically about a vertical line through the center of shield half 33'. Typically, the distance between the center of one hole 199 and any hole adjacent thereto is 0.125 inch.

Preferably, the diameter of all the holes 199 is the same. Preferably, all of the holes 199 have a diameter of less than 0.0625 inch and greater than 0.055 inch. Perhaps the most desirable value for the diameter of each of the holes 199 is about 0.059 inch.

If desired, the construction shown in FIG. 14 may be considered to be drawn to scale. The width of surface 44' in FIG. 14 may be 1.25 inches.

The embodiment of FIG. 15 may be further characterized as follows.

As will be described, as between two different fluids, such as nitrogen and methane, calibration can be saved if the holes 199 in FIGS. 14 and 15 are used with well 63 in FIG. 10. The operating frequency over a density of zero to 4 pounds per cubic foot may vary only 1 to 2 Hertz out of 314 Hz. or more.

Nitrogen is a fluid helpful in calibration because it may be easily obtained in a high degree of purity.

The portion of shield half 33' in FIGS. 14 and 15 having holes 199 therethrough may be described as "means providing an acoustical attenuator." This attenuator keeps $R_b = R_a$ as described hereinafter. It may have about an 80 percent transmission, if desired.

Well 63 may be described as "means providing an acoustical wave reflecting surface."

The differential equation defining the conditions for forced vibrations is as follows:

$$m \frac{d^2x}{dt^2} + c \frac{dx}{dt} + Kx = Q \sin \omega t \tag{1}$$

where
  $m$ is the effective mass of the vane, $c$ is the damping factor, $K$ is the vane spring constant,
  $x$ is the vane displacement, $t$ is time, $\omega$ is the radian frequency of the vane vibration, and
  $Q \sin \omega t$ is the forcing function of amplitude $Q$.

See volume 4, page 353 of the McGraw-Hill Encyclopedia of Science and Technology.

When there is a reflected wave from well 63 through, for example, nitrogen, the forcing function is $$Q \sin \omega t - Q_n \sin (\omega t + \phi_n) \tag{2}$$

where $Q_n$ is the amplitude of the reflected wave through nitrogen at the vane, and $\phi_n$ is the phase of the reflected wave at the vane.

From (2)

$$(Q - Q_n \cos\phi_n) \sin\omega t - Q_n \sin\phi_n \cos\omega t \tag{3}$$

If a calibration shift because of a change to methane is to be prevented, $$(Q - Q_n \cos\phi_n) \sin\omega t - Q_n \sin\phi_n \cos\omega t = (Q - Q_m \cos \phi_m) \sin\omega t - Q_m \sin \phi_m \cos\omega t \tag{4}$$

where the $m$ subscript denotes methane.
Thus, $$Q^2 - 2 QQ_n \cos \phi_n + Q_n{}^2\cos^2\phi_n + Q_n{}^2\sin^2\phi_n = Q^2 - 2 QQ_m \cos\phi_m + Q_m{}^2\cos^2\phi_m + Q_m{}^2\sin^2\phi_m \tag{5}$$

and $$R_n{}^2 - 2R_n \cos\phi_n = R_m{}^2 - 2R_m \cos\phi_m \tag{6}$$

where $$R_n = \frac{Q_n}{Q} \tag{7}$$

and $$R_m = \frac{Q_m}{Q} \tag{8}$$

$$\phi = \arctan \frac{-Q_o \sin \phi_o}{Q - Q_o \cos \phi_o} \tag{9}$$

where the subscripts denote either $n$ or $m$ and that $\phi$ should be the same for either case. Thus, see (12) and $$Q - Q_n \cos \phi_n = Q - Q_m \cos \phi_m \tag{10}$$

$$R_n \cos \phi_n = R_b \cos \phi_m \tag{11}$$

From (6) and (11)

$$R_m = \pm R_n \tag{12}$$

From (11) and (12), if $R_m = +R_n$ $$\phi_m = -\phi_n \tag{13}$$

To compute the approximate inside radius R of well 63, $$R = p\lambda_n + \frac{\phi_n \lambda_n}{2\pi} \tag{14}$$

where $p$ is a design integer $$\lambda_n = \frac{v_n}{f} \tag{15}$$

$$f = \frac{\omega}{2\pi} \tag{16}$$

and $v_n$ is the sonic velocity of nitrogen,
Thus, $$q\lambda_m + \frac{\phi_m \lambda_m}{2\pi} = p\lambda_n + \frac{\phi_n \lambda_n}{2\pi}$$

From (13) and (17)

$$q\lambda_m - p\lambda_n = \frac{\phi_n(\lambda_m + \lambda_n)}{2\pi} \tag{18}$$

$$\phi_n = \frac{(2\pi)(q\lambda_m - p\lambda_n)}{\lambda_m + \lambda_n} \tag{19}$$

From (14) and (19)

$$R = p\lambda_n + \left[\frac{q\lambda_m - p\lambda_n}{\lambda_m + \lambda_n}\right] [\lambda_n] \tag{20}$$

$$R = [\lambda_n] \left[p + \frac{q\lambda_m - p\lambda_n}{\lambda_m + \lambda_n}\right] \tag{21}$$

$$R = [\lambda_n] \left[\frac{(p+q)(\lambda_m)}{\lambda_m + \lambda_n}\right] \tag{22}$$

$$R = \frac{\lambda_m \lambda_n (p+q)}{\lambda_m + \lambda_n} \tag{23}$$

For R of a reasonable size where nitrogen and methane are concerned $$p + q = s \tag{24}$$

where $s$ is a positive integer. With nitrogen and methane, often $p = 1$ and $q = 0$, or vice versa.
Thus, $$R = \frac{s \lambda_m \lambda_n}{\lambda_m + \lambda_n} \tag{25}$$

or $$R = \frac{\lambda_m \lambda_n}{\lambda_n + \lambda_n} \quad (26)$$

when $s = 1$. (27)

If $R_m = -R_n$ (28)

in radians $\phi_m = \pm r\pi \pm \phi_n$ (29)

Thus, either $$R = \left[\frac{\lambda_n \lambda_m}{\lambda_n \pm \lambda_m}\right][q + p - r] \quad (30)$$

$$R = \left[\frac{\lambda_n \lambda_m}{\lambda_n \pm \lambda_m}\right][q + r - p] \quad (31)$$

where $r$ is any positive odd integer.

What is claimed is:

1. A vibration densitometer probe comprising: a body having a cylindrical shank with a first axis; a cylinder open at both of its ends and fixed to said shank in a position with a second axis perpendicular to said first axis; a vibratable vane fixed relative to said cylinder inside thereof located through said second axis and perpendicular to said first axis; a shield clamped to said shank and extending around said cylinder in spaced relation thereto, said shield having an end wall at least partially covering each of the ends of said cylinder, but located in spaced relation thereto, each of said end walls having perforations; and surface means fixed relative to said shield providing a surface to reflect waves in a fluid medium back through the perforations in both of said end walls to said vane.

2. The invention as defined in claim 1, wherein said end walls have acoustical impedances such that two reflected waves of the same frequency in fluids in which the waves move at different velocities reach the vane at approximately the same amplitude.

3. The invention as defined in claim 2, wherein said surface means is located at a distance from said vane such that the phases of said vane of said two waves reflected from said surface means are different but do not substantially change the resonant frequency of said vane when the space surrounding said vane is filled with one of said fluids and then the other, said vane being immersed in each respective fluid.

4. The invention as defined in claim 1, wherein said surface means is located at a distance from said vane such that the phases at said vane of two waves in two different respective fluids reflected from said surface means are different but do not substantially change the resonant frequency of said vane when the space surrounding said vane is filled with one of said fluids and then the other, said vane being immersed in each respective fluid, said reflected waves moving at two different respective velocities in said two fluids.

5. A densitometer probe comprising: a body having a shank portion; an assembly mounted on the end of said shank portion, said assembly including a vibratable member; and a shield fixed to the exterior of said body encasing said assembly, said shield having a hollow interior in which said assembly is located, said shield having at least two openings therethrough providing a restricted communication from the exterior thereof to the hollow interior thereof, said shank having an outer cylindrical surface with a first axis, said assembly having external and internal surfaces, both of which are approximately cylindrical and concentric with a second axis, said member including a thin vane which is an approximate right prism having a uniform rectangular cross section throughout its entire length, said shank having a fluid tight bond to said assembly at its lower end, said axes being perpendicular to each other, said vane being fixed to the interior of said assembly generally in a diametral plane perpendicular to said first axis, said shield being constructed in two vertically split substantially identical halves, means to clamp the bottom portions of said halves together, means to clamp said halves to said shank a short distance above said assembly, said assembly having a hole all the way therethrough defined by said internal surface thereof and uninterrupted except for said vane, said hole being open at both ends, said shield having first and second intersecting internal bores generally conforming to the shape of respective corresponding portions of the external cylindrical surfaces of said shank and said assembly, respectively, said first and second bores being generally concentric with said first and second axes, respectively, but being slightly but everywhere spaced from said shank and said assembly, respectively, so as not to touch the same, said shield having first and second parts of holes through the wall thereof near first and second opposite ends of the external cylindrical surface of said assembly, said holes being located generally in the plane of said vane, said holes having areas small in comparison to the cylindrical surface area plus the end surface areas of said second bore.

6. The invention as defined in claim 5, wherein said second bore is made in said shield halves so as to intercept and go part way through, but not all the way through said shield halves to provide said four holes therein.

7. A densitometer comprising: a probe including a body having a shank portion; an assembly mounted on the end of said shank portion; said assembly including a vibratable member; a shield fixed to the exterior of said body encasing said assembly, said shield having a hollow interior in which said assembly is located, said shield having at least two openings therethrough providing a restricted communication from the exterior thereof to the hollow interior thereof; a feedback loop connected from and to said probe to vibrate said member, said loop producing an output which is a function of the density of any fluid in which said assembly is immersed, said shank having an outer cylindrical surface with a first axis, said assembly having external and internal surfaces, both of which are approximately cylindrical and concentric with a second axis, said member including a thin vane which is an approximate right prism having a uniform rectangular cross section throughout its length, said shank having a fluid tight bond to said assembly at its lower end, said axes being perpendicular to each other, said vane being fixed to the interior of said assembly generally in a diametral plane perpendicular to said first axis, said shield being constructed in two vertically split substantially identical halves, means to clamp the bottom portions of said halves together, means to clamp said halves to said shank a short distance above said assembly, said assembly having a hole all the way therethrough defined by said internal surface thereof and uninterrupted except for said vane, said hole being open at both ends, said shield having first and second intersecting internal bores generally conforming to the shape of respective corresponding portions of the external cylindrical surfaces of said shank and said assembly, respectively, said first and second bores being generally concentric with said first and second axes, respectively, but being slightly, but everywhere spaced from said shank and said assembly, respectively, so as not to touch the same, said shield having first and second pairs of holes through the wall thereof near first and second opposite ends of the external cylindrical surface of said assembly, said holes being located generally in the plane of said vane, said holes having areas small in comparison to the cylindrical surface area plus the end surface area of said second bore.

8. The invention as defined in claim 7, wherein said second bore is made in said shield halves so as to intercept and go part way through, but not all the way through said shield halves to provide said four holes therein.

9. A vibration densitometer probe comprising: a body having a cylindrical shank with a first axis; a cylinder open at both of its ends and fixed to said shank in a position with a second axis perpendicular to said first axis; a vibratable vane fixed relative to said cylinder inside thereof located through said second axis and perpendicular to said first axis; and a shield clamped to said shank and extending around said cylinder in spaced relation thereto, said shield having an end wall at least partially covering each of the ends of said cylinder, but located in spaced relation thereto, each of said end walls being perforate, said end walls being substantially identical, each end wall having first and second sets of a plurality of cylindrical holes extending completely therethrough uniformly spaced in rows, each hole in one row lying in alignment with a corresponding hole in each of the other rows, said first set of holes having a row intermediate each adjacent pair of said second set of rows, two adjacent holes in one row having axes with one in an adjacent row which intercept a plane perpendicular thereto at the apexes of an equilateral triangle, each hole having the same diameter.

10. The invention as defined in claim 9, wherein each of said holes have a diameter of between about 0.0625 and 0.055 inch.

11. The invention as defined in claim 10, wherein each hole diameter is about 0.060.

12. A vibration densitometer assembly comprising: a base; means including a sidewall providing a chamber sealed except for one end opening toward and sealed to said base, a fluid exit hole, and at least a second hole through said sidewall adapted to, for example, face the flow of fluid in a pipeline at a first predetermined angle relative to the direction of fluid flow to permit fluid flow into and out of said chamber without turbulence; a vibration densitometer probe mounted on said base in said chamber, said probe having one end spaced from said base, said probe having a vibratable member extended downwardly through said means one end into said chamber in a position to be immersed in the fluid therein; and a shield fixed relative to said probe in a position inside said chamber partially surrounding said member to prevent a calibration shift, said means including a hollow cylinder providing said sidewall, and a circular disc closing the other end of said cylinder except for said fluid exit hole extending centrally therethrough, said second hole being generally circular and extending through said cylinder, said second hole having an axis in a plane perpendicular to the axis of said cylinder, said first predetermined angle being equal to +40°, said cylinder having an auxiliary generally circular hole therethrough the same diameter as that of said second hole and having an axis in said plane at a second predetermined angle of —80° relative to the axis of said second hole, said fluid exit hole being enerally circular and having a diameter less than that of said second and auxiliary holes, at least a portion of said second and auxiliary holes being located above the bottom of said member.

13. A vibration densitometer assembly comprising: a base; means including a sidewall providing a chamber sealed except for one end opening toward and sealed to said base, a fluid exit hole, and at least a second hole through said sidewall adapted to, for example, face the flow of fluid in a pipeline at a first predetermined angle relative to the direction of fluid flow to permit fluid flow into and out of said chamber without turbulence; a vibration densitometer probe mounted on said base in said chamber, said probe having one end spaced from said base, said probe having a vibratable member extended downwardly through said means one end into said chamber in a position to be immersed in the fluid therein; and a shield fixed relative to said probe in a position inside said chamber partially surrounding said member to prevent a calibration shift, said first predetermined angle being equal to 40°.

14. A vibration densitometer assembly comprising: a base; means including a sidewall providing a chamber sealed except for one end opening toward and sealed to said base, a fluid exit hole, and at least a second hole through said sidewall adapted to, for example, face the flow of fluid in a pipeline at a first predetermined angle relative to the direction of fluid flow to permit fluid flow into and out of said chamber without turbulence; a vibration densitometer probe mounted on said base in said chamber, said probe having one end spaced from said base, said probe having a vibratable member extended downwardly through said means one end into said chamber in a position to be immersed in the fluid therein; and a shield fixed relative to said probe in a position inside said chamber partially surrounding said member to prevent a calibration shift, said first predetermined angle being equal to +40°, said sidewall having an auxiliary hole therethrough at a second predetermined angle of —40° relative to the direction of fluid flow.

* * * * *